United States Patent
Burgeson et al.

[11] Patent Number: 6,153,593
[45] Date of Patent: Nov. 28, 2000

[54] LAMININ 5 AND THE FORMATION OF BASEMENT MEMBRANE STRUCTURE

[75] Inventors: Robert E. Burgeson, Marblehead, Mass.; Makoto Tsunenaga, Yokohama, Japan; Satoshi Amano, Komae, Japan; Toshio Nishiyama, Tokyo, Japan; Eijiro Adachi, Sagamihara, Japan; Nobuyuji Shioya, Yokohama, Japan

[73] Assignees: The General Hospital Corporation, Boston, Mass.; Shiseido Co., Ltd., Tokyo; University School of Medicine, Kahagawa, both of Japan

[21] Appl. No.: 08/868,600

[22] Filed: Jun. 4, 1997

Related U.S. Application Data

[60] Provisional application No. 60/018,950, Jun. 5, 1996.

[51] Int. Cl.[7] .............................. A01N 1/02; A61F 2/10; A61K 38/39; C12N 5/08
[52] U.S. Cl. ............................ 514/21; 435/1.1; 435/366; 435/402; 623/15
[58] Field of Search ................................... 530/350, 353, 530/356, 395, 842, 850, 851; 514/8, 12, 21; 435/1.1, 366, 371, 402; 623/15

[56] References Cited

U.S. PATENT DOCUMENTS

| | | | |
|---|---|---|---|
| 4,485,096 | 11/1984 | Bell | 424/532 |
| 5,352,668 | 10/1994 | Burgeson et al. | 514/21 |
| 5,514,364 | 5/1996 | Ildstad | 424/1.49 |
| 5,580,960 | 12/1996 | Burgeson et al. | 530/395 |
| 5,660,982 | 8/1997 | Tryggvason et al. | 435/6 |
| 5,770,562 | 6/1998 | Burgeson et al. | 514/8 |
| 6,034,068 | 3/2000 | Halberstadt | 514/21 |

OTHER PUBLICATIONS

J. Invest. Dermatol. vol. 108, No. 4, pp. 549,585. Abstract Nos. 70 (Coberly et al) and 288 (Tsunenaga et al), Apr. 1997.

*Primary Examiner*—Jeffrey E. Russel
*Attorney, Agent, or Firm*—Louis Myers; Fish & Richardson P.C.

[57] ABSTRACT

The use of laminin-5 to promote formation of basement membrane and to form skin equivalents and to improve grafting of keratinocyte sheets.

17 Claims, 4 Drawing Sheets

Control

Laminin-5

Control

Laminin-5

LAMININ 5 AND THE FORMATION OF BASEMENT MEMBRANE STRUCTURE

This application claims the benefit of U.S. Provisional patent application Ser. No. 60/018,950, filed on Jun. 5, 1996.

BACKGROUND OF THE INVENTION

The invention relates to the use of laminin 5 to induce or promote the formation, e.g., the in vivo formation, of basement membrane.

SUMMARY OF THE INVENTION

In general, the invention features, a method of promoting the formation of a basement membrane, preferably a complete basement membrane, between a substrate and a subject cell, e.g., an epidermal cell, which subject cell is preferably adhered to the membrane. The method includes: administering laminin 5, preferably purified laminin-5, at an interface between the substrate and the subject cell, e.g., a cell which is adhered to the substrate, thereby promoting basement membrane formation. Preferably the laminin-5 is administered in sufficient quantity and for a sufficient time to allow formation of a complete basement membrane or to substantially improve the morphology or frequency of the basement membrane over what would be present if exogenous laminin-5 was not administered.

In preferred embodiments: the subject cell is an epidermal cell, e.g., a keratinocyte; the subject cell is adhered to the membrane.

In preferred embodiments, the cell is a cell in a sheet of cells, e.g., autologous or allogenic cells, e.g., cells which have been cultured in vitro.

In preferred embodiments the laminin-5 is administered at initial level of at least 0.5, more preferably 1.0 2.0, 10.0, 50, 100, $\mu g/cm^2$ of substrate.

In preferred emodiments the level of laminin-5 administered is maintained for at least 1, 3, 5, one week, 10, 15, or 30 days.

In preferred embodiments the laminin-5 is administered subsequent to a previous administration wherein said previous administration promotes the adhesion of the cell to a substrate.

In preferred embodiments the substrate is an in vitro substrate, e.g., the surface of a device or surgical appliance, or is an in vitro substrate on which a skin product or skin substitute is cultured.

In preferred embodiments the substrate is an in vivo substrate, e.g., a second cell, e.g., a mesynchymal cell.

In preferred embodiments the substrate is a wound surface, a burn surface, a corneal surface, a graft surface, a dermal surface, the surface of liver, pancreas, tooth or gum tissue.

In preferred embodiments the laminin-5 is administered after attachment of the subject cell to the substrate or to the basement membrane or nascent basement membrane.

In preferred embodiments repeated administrations of laminin-5 are administered.

In preferred embodiments sufficient laminin-5 is administered to increase the quality of the basement membrane substantially over what would be seen in the absence of exogenously applied laminin 5. In preferred embodiments the amount of laminin-5 administered is sufficient to increase the basement membrane morphology or frequency score, as described herein, by at least 20, 50, 75, 100, 200, or 500%.

In another aspect, the invention features, a method of producing skin equivalents in vitro. The method includes: provided a contracted substrate; culturing cells, e.g., keratinocytes, on the substrate in the presence of exogenously added laminin-5 to thereby produce a skin equivalent.

In preferred embodiments the contracted substrate is, e.g., a fibroblast-contracted substrate, e.g., , a fibroblast-contracted gel substrate.

A purified preparation of a peptide or protein is a preparation which is substantially free of at least one of the peptides or proteins the subject molecule naturally occurs with in a cell. A purified preparation of a non-naturally occurring peptide is one which is at least 10% by weight of the subject peptide or protein.

A complete basement membrane is one which includes one, two, three, or more of the following: a continuous lamina densa; a lamina lucida; hemidesmosomes which are normal or substantially normal in morphology, number, and distribution; and anchoring fibrils which are, normal or substantially normal in morphology, number, and distribution.

The inventors have shown that the administration of exogenous laminin-5 can promote the formation of a complete and ultrastructurally normal basement membrane. The inventors have developed organotypic cultures of human keratinocytes and dermal fibroblasts for the production of skin equivalents. The keratinocytes can be grown upon fibroblast-contracted collagen gels. In the culture, keratinocytes and fibroblasts derived from human neonatal or adult skin produce basement membrane components and these molecules are deposited at the interface of keratinocytes and collagen gels.

The methods of the invention can be used in promoting basement membrane formation, to establish the skin equivalents, and to elucidate the mechanism of assembly for basement membrane zone. Laminin 5 was identified as the anchoring filament protein. To function as a bridge structure between the keratinocyte and the basement membrane, laminin 5 must interact with components of the basement membrane and with its cell surface binding proteins. The effect of laminin 5 on the formation of basement membrane structure in the skin equivalents is described herein.

Other features and advantages of the invention will be apparent from the following description and from the claims.

DETAILED DESCRIPTION

DRAWINGS

The drawings are first briefly described.

Figure 3A:
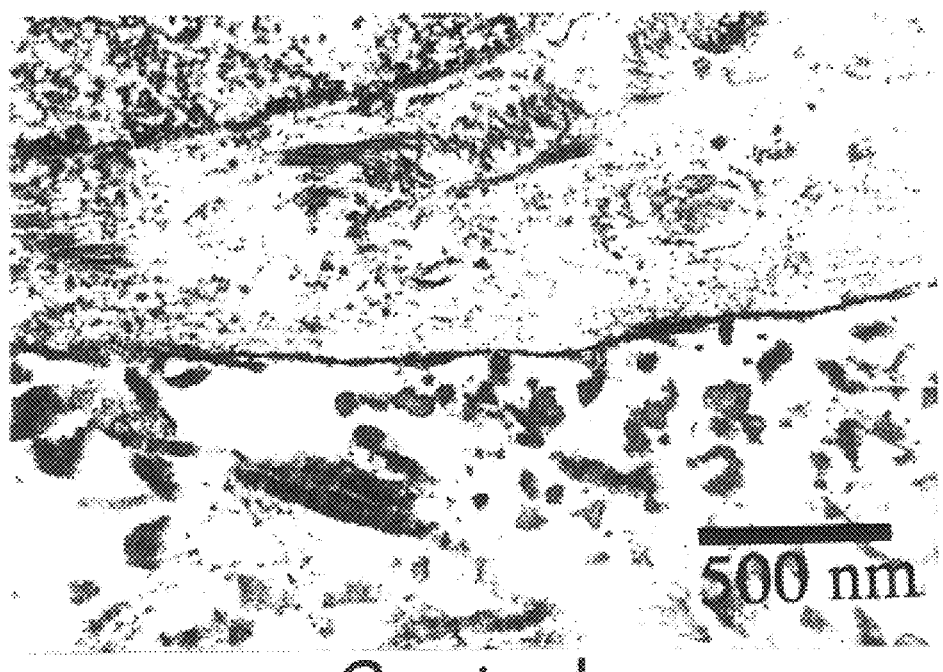

FIG. 3A (control) and 3B (laminin-5) are depictions of basement membrane structure.

Figure 4A:
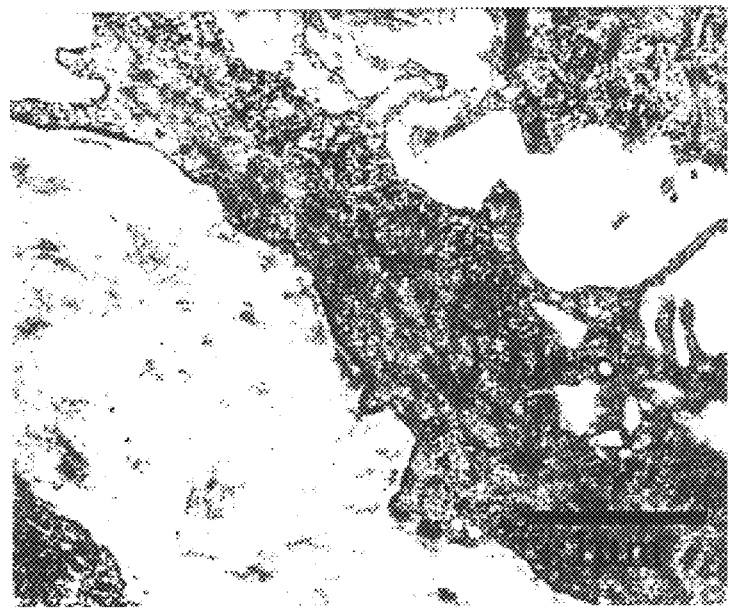
Figure 4B:

FIG. 4A (control) and FIG. 4B (laminin 5) show the in vivo effect of laminin 5 on basement membrane formation.

IN VITRO SKIN EQUIVALENTS

Skin equivalents (human foreskin keratinocytes and fibroblasts) were cultured for a week in standard culture medium for organotypic culture. The skin equivalents were cultured for an additional one week in the culture medium with (1) 5 $\mu g/ml$ laminin 5. The medium was renewed every other day. After 2 weeks culture, the ultrastructure of the dermal-epidermal junction in vitro was determined by electronmicroscopy.

Figure 1:
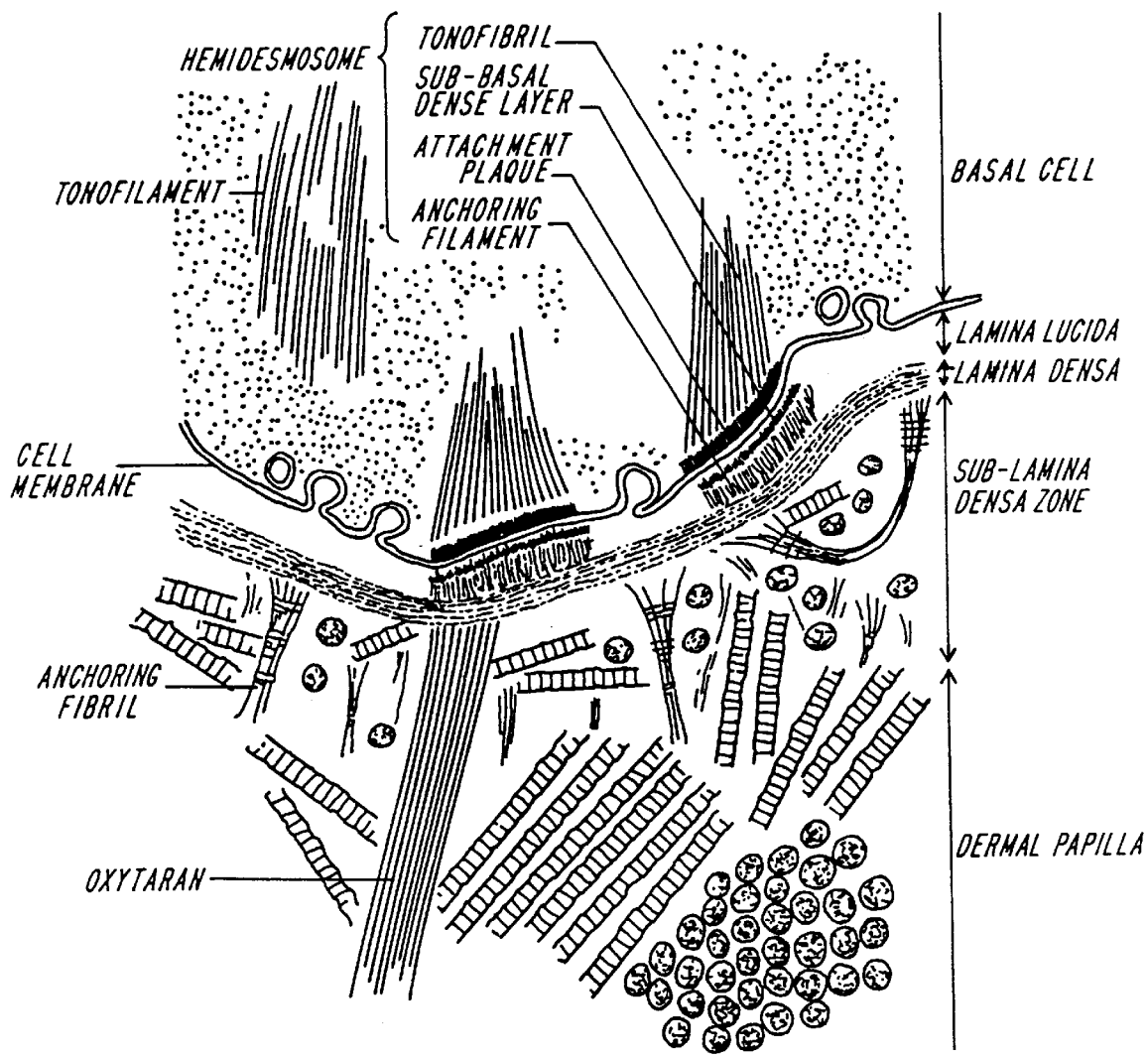
FIG. 1 is a diagram of the deramo-epidermo junction model.
Figure 3B:
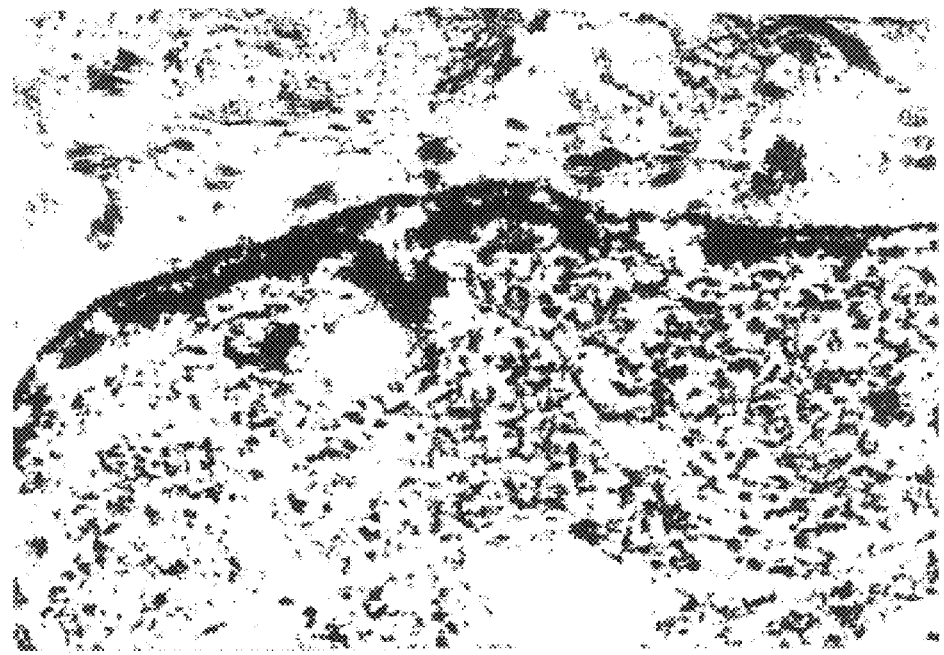

The recognizable structure of basement membrane (FIG. 1), such as lamina densa, lamina lucida, hemidesmosomes and anchoring fibrils, were detected, but only slightly, in the control culture (FIG. 3A). In contrast to the results with the control culture, recognizable and classic structures of the basement membrane, such as continuous lamina densa, lamina lucida, hemidesmosomes, were frequently detected in the skin equivalents cultured with laminin 5 (5 µg/ml) (FIG. 3B). Data from the first experiment, which were confirmed by determining scores of the basement membrane structure morphometrically, are indicated in Table 1 below.

TABLE 1

Score of basement membrane quality

|  | Control | Laminin-5 |
|---|---|---|
| First Experiment | 1.6 | 2.7 |
| Second Experiment | 4.7 | 8.8 |

Figure 2:
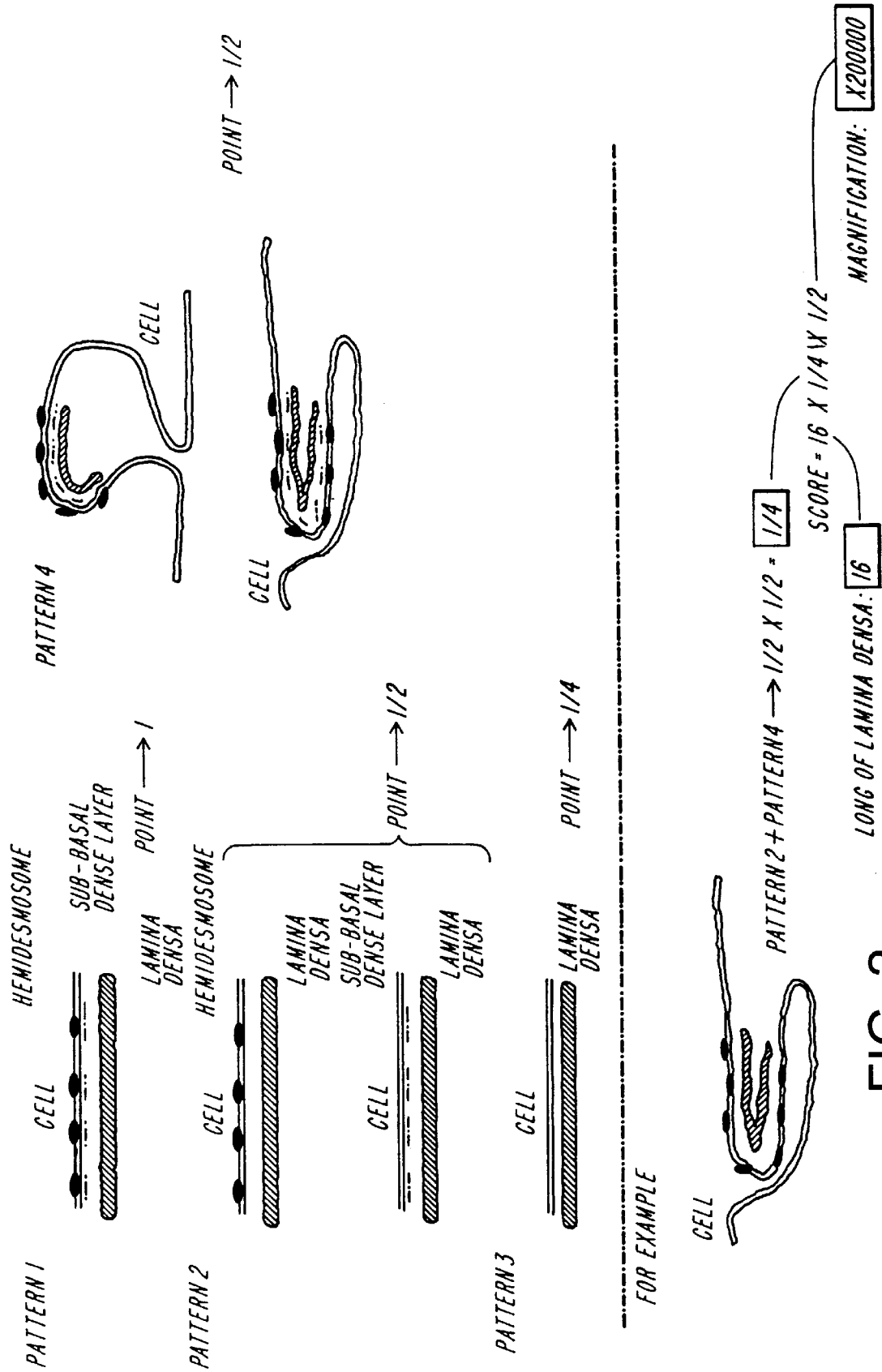
FIG. 2 is descriptions of the basement membrane scoring system used herein.

The quality of the basement membrane formation was expressed by scores. The scores were calculated by determining the formation pattern as is shown in FIG. 2. The results indicate that laminin 5 promotes basement membrane formation. The frequency of the basement membrane structure on the culture with laminin 5 was higher than that of control. The effect of laminin 5 was reconfirmed in a second experiment.

While not wishing to be bound by theory, it is possible that laminin 5 added to the culture medium binds to its receptor in the keratinocyte plasma membrane and limits the diffusion of certain basement membrane components from keratinocytes and fibroblasts, and stabilizes the assembly of the molecules sufficiently so that ultrastructural formation of these molecules can occur.

In vivo Transplantation of Cultured Keratinocyte Sheets

Autologous transplantation of cultured human keratinocyte sheets has been used clinically for the treatment of extensive burns, giant nevus, and other disorders. In practice, the rate of take of the sheets transplanted directly to granulation tissue without dermal components has been less than optimal. The inventors have provided improved methods of grafting.

The effect of laminin 5 upon the efficiency of transplantation of keratinocyte sheets to nude mice was followed in the following experiment. Keratinocyte sheets were prepared according to the method of Rheinwald and Green. In group 1 (laminin 5: mice n=12; rats n=15), purified laminin 5 was added to the sheets (1.0 µg/cm²). DMEM alone was added to group 2 (control: mice n=12; rats n=15). The sheets were grafted to the panniculus carnosus of nude mice (Balb/c nu/nu) (n=12) and to nude rats (Fisher 344) (n=15). The take rate was assessed by photometric measurement of the area of surviving epithelium at 7 days post grafting by NIH image analysis Sections were prepared for examination by immuno-histochemistry and electron microscopy.

Laminin 5 bound the coated keratinocyte sheets. At 7 days post grafting, the area of epithelization of group 1 was significantly larger than that of group 2, as shown in Table 2.

TABLE 2

The percentage of graft take of cultured human keratinocyte sheets

|  | pretreatment with laminin 5 | control |
|---|---|---|
| nude mice (n = 12) | 58.5 ± 21.9* | 38.8 ± 30.5 |
| nude rats (n = 15) | 53.1 ± 20.9** | 35.3 ± 22.5 |

The values are the mean ± SD.
*;P < 0.05.
**;P < 0.01.

Collage IV, laminin 5 and collagen VII stained more strongly (by immuno-chemical staining) at the dermal-epidermal junction in group 1 than in group 2. Integrin chains α6 and β4 were similar in both groups. At day 3 after grafting the lamina densa of group 1 grafts were more continuous relative to group 2 when the well-grafting areas were examined as shown in FIG. 4. At day 7 after grafting, the basement membrane formation in group 1 is identical as compared to the control. When scored by the system of FIG. 2 the control was 3.9 and the laminin-5 trial was 20.3.Thus, pretreatment of cultured human keratinocyte sheets with laminin 5 improved the extent of epithelial coverage and increased the rate of neobasement membrane formation.

These experiments are described in more detail below.

Cultured epidermal sheets with laminin 5 were prepared as follows. Human skin keratinocytes were cultured using a 3T3 feeder layer in a keratinocytic growth medium which was prepared according to the method reported by Rheinwald and Green. The keratinocyte sheets were detached from dishes using dispase. The sheets were washed and then placed onto a aterocollagen sheet for the carrier. Purified laminin 5 in DMEM (1 µg/ml) was added onto the sheets. After incubation the sheets were washed with Hank's solution.

Epidermal sheets were drafted as follows. Skin flaps (1.5 cm square) of nude rats or nude mice were elevated and full thickness skin defects were made in the backs. The cultured epidermal sheets were grafted on the panniculus carnosus. Silicone gauze was applied over the sheets, then the skin flap was replaced on, and the margin was sutured. The take rate was assessed by photometric measurement of the area of existing the epidermal sheets 7 days after grafting. Mean values of the areas were analyzed by NIH image system.

Statistical analysis was performed as follows. All data were expressed as the mean and standard error (SEM). Comparison between means in each group were performed by t-test (Statview). Differences having a P value <0.05 were considered significant.

Histological examination and immunohistochemistry were performed as follows. The skin pieces were fixed by AMeX method. Briefly, the pieces were incubated overnight in acetone at −20° C. The pieces were placed in acetone and incubated for 15 min at 4° C. and then for 15 min at RT. The pieces were incubated twice with methyl benzoate for 15 min at RT and twice with xylene for 15 min at RT. After the incubation with solvent, the skin pieces were incubated with paraffin for 3 hours at 60° C.

Paraffin sections were deparaffinized with xylene, immediately immersed twice in acetone, and washed with PBS, followed by immunostaining by using streptavidiniotinylated-peroxidase complex (SAB) method with monoclonal antibodies listed below.

| | |
|---|---|
| Laminin 5 (BM165) | 2 μg/ml |
| Collagen IV (JK199) | culture sup. (1:5) |
| Collagen VII (NP185) | 6 μg/ml |
| Integrin α6 (Chemicon Int. Co.) | 1:100 |
| Integrin β4 (Chemicon Int. Co.) | 1:100 |

The sections were incubated with 2%NSS (normal swine serum) for 20 min, then primary antibodies were added and incubated overnight at 4° C. The sections were rinsed with PBS and incubated with biotinylated anti-mouse IgG (1:200, Vector Lab. Inc.) for 1 hour at RT. They were incubated with SAB (1:100, Amersham) for 1 hour at RT. After rinsing with PBS, the sections were incubated in solution of DAB (diaminobenzodine) for 5 min. Nuclear counterstaining was performed with Carazzi hematoxylin solution.

Electronmicroscopy was performed as follows:

For electron microscopy, the grafted skins were excised with the surrounding tissue and fixed with 2% glutaraldehyde in 0.1 M cacodylate buffer, pH 7.4, then post fixed with 1% OsO4 in 0.1 M cacodylrate buffer, dehydrated through an ethanol series, and embedded in Quctol 812 (Nissin EM Co., Ltd., Japan). Ultra thin sections were prepared with an ultramicrotome (Portor-Blum MT-IIB or LKB NOVA), stained with uranyl acetate and lead citrate, and examined under a JEM-100SX or H-600 electron microscope.

The results are shown in Table 2.

Other Embodiments

Laminin 5 is described in the invention also includes the use of any biologically active fragment or analog of a laminin-5 protein. By "biologically active" is meant possessing any in vivo or in vitro activity which is characteristic of laminin-5, e.g., laminin-5 activity as described above. A laminin-5 protein fragment or analog possesses, most preferably 90%, preferably 40%, or at least 10%, of the activity of a naturally occurring laminin-5 isoform in any in vivo or in vitro laminin-5 assay.

Preferred analogs include laminin-5 peptides or recombinant laminin-5 proteins or peptides (or biologically active fragments thereof) whose sequences differ from the wild-type sequence by one or more conservative amino acid substitutions or by one or more non-conservative amino acid substitutions, deletions, or insertions which do not abolish biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-I,eu, Ile, D-Ile, Met, D-Met |

Other useful modifications include those which increase peptide stability; such analogs may contain, for example, one or more non-peptide bonds (which replace peptide bonds) or D-amino acids in the peptide sequence.

Analogs can differ from a naturally occurring laminin-5 protein in amino acid sequence or can be modified in ways that do not affect sequence, or both. Analogs of the invention will generally exhibit at least 70%, more preferably 80%, more preferably 90%, and most preferably 95% or even, 99%, homology with a segment of 20 amino acid residues, preferably more than 40 amino acid residues or more preferably the entire sequence of naturally occurring laminin-5 protein sequence.

Alterations in primary sequence include genetic variations, both natural and induced. Also included are analogs that include residues other than naturally occurring L-amino acids, e.g., D-amino acids or non-naturally occurring or synthetic amino acids, e.g. β or γ amino acids. Alternatively, increased stability may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

Other embodiments are within the following claims.

What is claimed is:

1. A method of promoting the formation of a basement membrane between a substrate and a subject cell, comprising: administering laminin-5, at an interface between the substrate and the subject cell which is adhered to the basement membrane, thereby promoting basement membrane formation, and provided that the laminin-5 is administered in sufficient quantity and for a sufficient time to: allow formation of a complete basement membrane or to substantially improve the morphology or frequency of the basement membrane over what would be present if exogenous laminin-5 was not administered.

2. The method of claim 1, wherein said cell is an epidermal cell.

3. The method of claim 1, wherein said cell is a keratinocyte.

4. The method of claim 3, wherein said cell is in a sheet of cells.

5. The method of claim 4, wherein said cell is autologous cells which have been cultured in vitro.

6. The method of claim 1, wherein said laminin-5 is administered in an amount sufficient to increase the frequency of basement membrane structure by at least 20%.

7. A method of producing skin equivalents in vitro comprising: providing a fibroblast-contracted gel substrate; culturing cells which are adhered to the substrate in the presence of exogenously added laminin-5 to thereby produce a skin equivalent having a complete basement membrane or a substantially improved morphology or frequency of basement membrane over what would be present if exogenous laminin-5 was not present.

8. The method of claim 7, wherein the cell is an epidermal cell.

9. The method of claim 7, wherein the cell is a keratinocyte.

10. The method of claim 9, wherein said laminin-5 is administered at a level that is maintained for at least one week.

11. The method of claim 7, wherein said laminin-5 is administered in an amount sufficient to increase the frequency of basement membrane structure by at least 20%.

12. A method of grafting cultured keratinocyte sheets in vivo comprising:

providing a keratinocyte sheet;

grafting said sheet on a panniculus carnosus of a subject in the presence of exogenously added laminin-5, said laminin-5 being present at a concentration sufficient to improve the extent of epithelial coverage over what would be present if exogenous laminin-5 was not administered and to promote formation of a complete basement membrane.

13. The method of claim 12, wherein said sheet comprises autologous cells.

14. The method of claim 12, wherein said sheet has been cultured in vitro.

15. The method of claim 14, wherein said laminin-5 is administered at an initial level of at least $0.5 \mu g/cm^2$ of a substrate.

16. The method of claim 12, wherein said laminin-5 is administered at a level that is maintained for at least one week.

17. The method of claim 12, wherein said laminin-5 is administered in an amount sufficient to increase the frequency of basement membrane structure by at least 20%.

* * * * *